United States Patent [19]
DeBord et al.

[11] Patent Number: 5,824,813
[45] Date of Patent: Oct. 20, 1998

[54] LAYERED VANADIUM OXIDE COMPOSITIONS

[75] Inventors: Jeffrey Robert Douglas DeBord, Hightstown; Robert C. Haushalter, Little York; Yiping Zhang, Plainsboro, all of N.J.

[73] Assignees: NEC Research Institute, Inc., Princeton, N.J.; Texas A&M University, College Station, Tex.; Syracuse University, Syracuse, N.Y.

[21] Appl. No.: 961,857

[22] Filed: Oct. 31, 1997

Related U.S. Application Data

[62] Division of Ser. No. 729,473, Oct. 11, 1996, Pat. No. 5,717,120, which is a division of Ser. No. 490,161, Jun. 14, 1995, Pat. No. 5,659,034.

[51] Int. Cl.$^6$ ............... C07F 15/00; C07F 1/08; C07F 3/06; C07F 15/02
[52] U.S. Cl. ............... 556/28; 556/42; 556/110; 556/118; 556/138; 556/511
[58] Field of Search ............... 556/28, 42, 110, 556/118, 138, 511

[56] References Cited

U.S. PATENT DOCUMENTS 5,324,848  6/1994  Haushalter et al. ............... 556/13

*Primary Examiner*—Mukund J. Shah
*Assistant Examiner*—Tamthom T. Ngo
*Attorney, Agent, or Firm*—Arthur J. Torsiglieri; Jeffery J. Brosemer

[57] ABSTRACT

A number of layered vanadium oxide crystalline compositions are prepared by simple hydrothermal reactions. Generally, the compositions comprise parallel layers of mixed valence vanadium oxides with guest cations intercalated between the layers. The guest cations may comprise metal coordination complexes with bidentate ligands, monomeric ammonium or diammonium cations, or mixtures of alkali metal cations with monomeric ammonium cation or diammonium cations.

1 Claim, No Drawings

LAYERED VANADIUM OXIDE COMPOSITIONS

This is a division of application Ser. No. 08/729,473 filed Oct. 11, 1996, which is a divisional application Ser. No. 08/490,161 filed Jun. 14, 1995, U.S. Pat. No. 5,659,034.

FIELD OF THE INVENTION

This invention relates to vanadium oxide crystalline compositions and more particularly to such compositions in which the vanadium oxide forms two dimensional layers between which are intercalated guest cations.

BACKGROUND OF THE INVENTION

There has been growing interest in vanadium compounds of various types for use as catalysts in a variety of chemical procedures. There also has been particular interest in vanadium oxides for use in electronic devices for heat sensing.

There has also been growing interest in layered structures, typically for use as hosts to support guest cations intercalated between the layers. In particular, layered inorganic oxides constitute a diverse class of materials most of which share the common structural feature of a cationic guest which lies between the anionic oxide layers. The largest number of examples known are layered materials composed largely of main group cations like clays, but solids with transition or post-transition elements like the layered double hydroxides and certain alkali metal titanates are also known. Layered oxides hosting both transition and main group cations, such as the Zr, V and Mo phosphates and phosphonates, have also been studied. While many of these solids are noted for their unique characteristic of allowing a wide variety of organic or inorganic chemistries to be performed in the interlamellar region, the closed shell diamagnetic layers serve mainly as an inert nanoscale scaffolding. In contrast to these diamagnetic layers, several lamellar vanadium oxide solids have been prepared by the intercalation of both alkali metal cations and conductive organic polymers between layers of $V_2O_5$.

The present invention represents novel forms of such layered structures involving vanadium oxides.

SUMMARY OF THE INVENTION

The present invention provides compositions of the generic formula

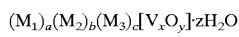

in which the layered mixed-valence vanadium oxide forms host layers between which are intercalated either a) cationic transition or post-transition metal coordination complexes, b) monomeric ammonium or diammonium cations, or c) a mixture of alkali metal cations and monomeric ammonium or diammonium cations.

In the generic formula, $M_1$ is a metal-coordination complex $[L_nA]^{+w}$, where L is a bidentate amine ligand, A is a transition or post-transition metal, n is equal to 1, 2 or 3, and w is 1, 2, 3 or 4. When a is other than zero, b and c are zero. When b has a non-zero value, a is equal to zero and c may or may not have a non-zero value. When c has a value, $M_3$ is an alkali metal cation.

More complete descriptions of $M_1$, $M_2$ and $M_3$ and particular examples of each will be provided in the more detailed description.

DETAILED DESCRIPTION OF THE INVENTION

As set forth above, the generic formula of compositions provided by the invention is

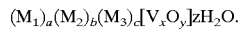

As mentioned above, $M_1$ is a metal coordination complex given by $[L_nA]^{+w}$, where the bidentate ligand L is a diamine of the form $R_2N(C_mH_{2m})NR_2$, or an aromatic diamine. R, as is familiar to the art, corresponds to $C_pH_{2p+1}$ where $1 \leq m \leq 4$, $0 \leq p \leq 4$, the metal A is a transition or post-transition metal, preferably either Ni, Cu, or Zn, and w is an integer from 1 to 4.

The group in which the guest cations are solely interlayer transition or post-transition metal coordination complexes $M_1$ will be described as the first group of the generic formula.

The compositions of this first group of the generic formula, corresponding to b and c equal to zero in the generic formula, have been prepared, for example, in a single step by the reaction of a transition or post-transition element source, a bidentate amine and $V_2O_5$ in water sealed in a 23-ml poly(tetrafluoroethylene) lined acid digestion bomb and heated in the 170°–200° C. range and are isolated as highly crystalline, typically thin black plates. Since no external reducing agent is employed, the amine presumably serves as the reducing agent. The materials, $(L_2M)_y[VO_x]$ with L=bidentate amine, M=Cu, Ni or Zn, $0.16 \leq y 0.33$ and $2.33 \leq x \leq 2.83$, share common structural features of a mixed valence $V^{4+}/V^{5+}$ oxide layer as well as a six coordinate interlayer cation with four of the six coordination sites occupied by N atoms from two bidentate amine ligands and two sites from O atoms of the VO layer. The layers are built up in all cases from $VO_5$ square pyramids and $VO_4$ tetrahedra connected by edge and corner sharing interactions.

As an example of the preparation of a compound of the first group, there was heated together at a temperature of 170° C. for 44 hours and then at 200° C. for 112 hours a mixture of 0.312 gram of $V_2O_5$, 0.049 gram of ZnO, 10 milliliters of $H_2O$ and 0.325 gram of 2,2'-dipyridyl. After such treatment, there was filtered a mixture of brown chunks of $[(bipy)_2Zn]_2[V_6O_{17}]$ and black rod-shaped crystals of $VO(VO_3)_6[VO(bipy)_2]$, where (bipy)=2,2'-dipyridyl, and a small amount of unidentified green powder.

The structure of the compound $[(bipy)_2Zn]_2[V_6O_{17}]$, which is to be designated as Compound 1, consists of VO layers, which, when viewed parallel to [100], display a very pronounced sinusoidal ruffling with an amplitude of ca. 13 Å and a period of ca. 15 Å. These layers are composed solely of $V^{5+}O_4$ tetrahedra, each of which has a terminal vanadyl (V=O) group and shares three corners with three neighboring $VO_4$ units. Within each VO layer there are very large, roughly circular rings, which alternately lie in planes approximately parallel to (011) and ($\bar{1}$1), defined by fourteen $VO_4$ tetrahedra with a transannular V—V distances near 13 Å. There are two Zn atoms per ring, on either side of the $\bar{1}$ site in the center of the ring, each bonded in a cis fashion to two oxygen atoms from two second nearest neighbor $VO_4$ groups on opposite sides of the ring. The two Zn atoms have bipy ligands that protrude above and below the mean plane of the $V_{14}$ ring and fill the troughs created from the ruffling of the layers with the organic ligands.

The use of ethylenediamine (en) as a bidentate ligand has allowed not only the isolation of several new one dimensional (1-D) Cu-en-VO materials but several layered solids as well. Two layered examples form the en system are the isctypic, mixed valence $V^{4+}/V^{5+}$vanadium oxides (en)$_2$Zn[V$_6$O$_{14}$]and (en)$_2$Cu[V$_6$O$_{14}$] to be designated Compounds 2 and 3, respectively. Compound 2 was prepared by mixing 0.192 (g) of V$_2$O$_5$, 0.042 (g) of ZnO$_1$ 10 (ml) of H$_2$O and 0.2 (ml) of en and heating to 170° C. for 66 hours. Compound 3 was prepared by heating 170° C. for 65 hours a mixture of 0.17 (g) of copper chloride dihydrate, 0.181 (g) of V$_2$O$_5$, 0.28 (ml) of en and 8 (ml) of water. Both materials contain Cu or Zn in a distorted MO$_2$N$_4$ octahedral environment coordinated to four N donor atoms, which lie approximately in a plane parallel to the VO layers, and two trans O atoms from two adjacent layers, coordinated via very long M—O interactions. While this nearly square planar coordination is not atypical for the Cu in Compound 3 (four N at ≈2.07 Å; two O at 2.53 Å), it is unusual for the Zn found in Compound 2 (two N at 2.12 Å and two at 2.07 Å; two O at 2.45 Å). The VO layers in Compounds 2 and 3 contain infinite zig-zag chains of edge-sharing V$^{4+}$O$_5$ square pyramids running parallel to [010], with their terminal vanadyl groups oriented in pairs toward opposite sides of the layer, connected together by V$^{5+}$O$_4$ tetrahedra giving a layer composition of [(V$^{5+}$)$_2$(V$^{4+}$)$_4$O$_{14}$]$^{2-}$ according to valence sum calculations. Surprisingly, in spite of the fact that ⅔ of the V atoms are in the 4+ oxidation state (d$^1$), Compound 2 does not give an ESR signal and is nearly diamagnetic according to preliminary magnetization measurements that show that $\chi$=M/H actually decreases in the range 150<T<300K. Compound 3 also appears to have layers with suppressed magnetic moments with $\mu_{eff}$(300K)~2.2 BM($\mu_{eff}$=[8$\chi$T]½) only slightly greater than that expected (~1.8 BM) for the Cu$^{2+}$ (S=½). Below room temperature, the moment slowly decreases and reaches the value expected for only the Cu$^{2+}$ by ~70K and below this temperature $\chi^{-1}$(T) is linear (unlike T>70K with a $\theta$ near zero indicative of a paramagnet. The magnetic data for Compounds 2 and 3 imply that either the layers have already undergone an antiferromagnetic phase above room temperature or the spins are paired within states that are delocalized within the layers.

Changing the reaction conditions in the en/Cu$^{2+}$V$_2$O$_5$ system gives rise to other vanadium oxides with ligated Cu bound to the layers, such as [(en)$_2$Cu]$_2$[V$_{10}$O$_{25}$], to be designated as Compound 4. This was prepared by heating at 170° C. for 42 hours a mixture of 0.51 (g) of cooper chloride dihydrate, 0.18 (g) of V$_2$O$_5$, 0.45 (ml) of en and 8.0 (ml) of water. Like Compounds 2 and 3, Compound 4 has a nearly square planar (en)$_2$M$^{2+}$(M=Cu) cation bonded to two trans oxygen atoms from two adjacent layers which are formulated as [(V$^{5+}$)$_6$(V$^{4+}$)$_4$O$_{25}$]$^{4-}$ according to valence sum calculations. The layers are built up from double strands of infinite corner sharing strings of edge-sharing trimeric VO$_5$ square pyramids, which run parallel to [001] and are connected together by VO$_4$ tetrahedra. The double strands are in turn bridged together by additional VO$_4$ tetrahedra to create a layer containing ordered voids with O—O diameters of 6 Å. Magnetization data shows that $\mu$(300K)~5.5 BM which is well below that expected for the six unpaired spins from 2 Cu$^{2+}$ and 4 V$^{4+}$. The moment decreases nearly linearly over the entire range 20K<T<300K and reaches a value of ca. 2.8 BM near 10K which is the moment expected for two Cu$^{2+}$(S=½) centers. Below ca.15k, $\chi^{-1}$(T) is linear with a $\theta$0 near zero consistent with paramagnetism. Thus the magnetic behavior of Compound 4 resembles that of Compound 3 in that the layers have magnetic moments that slowly decrease over large temperature intervals, with no characteristic anomalies indicative of a phase transition, and appear essentially diamagnetic at very low temperatures.

As mentioned previously, another major group of the generic formula corresponding to a and c equal to zero in the generic formula, to be designated group 2, consists of organically templated mixed-valence vanadium oxides. In this second group, M$_2$ is an organic cation taken from the group consisting of R$_4$N$^+$, cyclic ammonium or polyammonium cations [Q$_{4-p}$N(C$_n$H$_{2n}$)$_p$NQ$_{4-p}$]$^{+f}$ where $1 \leq p \leq 3$ and Q=R, C$_6$H$_5$ or (C$_n$H$_{2n}$)N$^+$R$_3$ with $1 \leq n \leq 4$, and R is C$_m$H$_{2m+1}$ or C$_6$H$_5$, where m=0$\leq$m$\leq$4 and f is the number of N atoms in the cyclic ammonium or polyammonium cation.

An example of this group 2 is (H$_3$N(CH$_2$)$_3$NH$_3$)[V$_4$O$_{10}$] to be designated Compound 5. Black plate-like crystals of Compound 5 were prepared from the hydrothermal reaction of 0.296 (g) of V$_2$O$_5$, 2.0 (ml) of 1.0M HCl, 0.2 (ml) of (dap) and 10 (ml) of H$_2$O at 170° C. for 66 hours, where (dap) is 1,3-diaminopropane.

A single crystal X-ray diffraction study of Compound 5 revealed the novel vanadium oxide layers with propanediammonium dications occupying the interlamellar space. The layers are constructed from equal number of VO$_4$ tetrahedra and VO$_5$ square pyramids. While VO$_4$ tetrahedra are isolated from each other, the VO$_5$ square pyramids exist in pairs sharing one edge. Within a pair of square pyramids, the two apical oxygen atoms are oriented toward opposite sides of the plane of the layer. Each pair of the pyramids is linked to six VO$_4$ tetrahedra via corner-sharing, forming two dimensional layers. There are four independent V sites in this structure. While the atoms V(1) and V(4) have a distorted square pyramidal configuration, the atoms V(2) and V(3) are in fairly regular tetrahedral coordination environment. The V—O bond distances of V(2)O$_4$ tetrahedron are in the range of 1.648 (4)–1.826 (4) Å, and bond angles in the range of 106.0(2)°–113.2(2)°. The V(3)O$_4$ tetrahedron has bond distances in the range of 1.643(5)–1.834(4) Å, and bond angles in the range of 107.6(2)°–111.3(2)°. The V(1)O$_5$ square pyramid has the shortest bond distance of 1.612(4) Å formed with the vanadyl oxygen O(9), and the rest of the four V—O bond distances in the range of 1.912(4)–1.967(4) Å. The V(4)O$_5$ square pyramid has its vanadyl oxygen O(7) at a distance of 1.603(4) Å, and the other four oxygen atoms at distances in the range of 1.924 (4)–1.974 (4) Å. While the square pyramidal vanadium has an oxidation state of +4, the tetrahedral vanadium is indicative of an oxidation state of +5. This assignment of oxidation state is consistent with the overall charge balance of the compound and confirmed by the valence sum calculation which gave a value of 4.1 for V(1) and V(4), and 4.8 for V(2) and V(3). There is an extensive hydrogen bonding network formed among the —NH$_3^+$ groups of the propanediammonium cations and the terminal oxygen atoms (O(6), O(7), O(9), O(10) from the oxide layers above and below. This extensive hydrogen bonding motif causes the organic components to be released only at elevated temperatures. Thermogravimetric analysis (TGA) at a heating rate of 10° C./min. under N$_2$ showed no weight loss until ca. 300° C. where the release of the organic component commences.

There has been a great deal of interest in vanadium bronzes M$_x$V$_2$O$_5$, especially lithium vanadium bronzes Li$_x$V$_2$O$_5$, because of their interesting electronic properties and potential applications in high energy batteries. The oxide layers in the structures of Compound 5 are similar to those in the structure of CsV$_2$O$_5$, described in Acta Cryst 1977, B33, 789 by K. Walterson et al, where the Cs$^+$ cations lie between the vanadium oxide layers. Compound 5 is believed to represent the first example of a new class of materials organically based vanadium bronzes. One would expect that new vanadium oxide structure types can be made by introduction of organic templates of different sizes and charges. In fact, we have isolated several new layered vanadium oxides containing different organic cations including α- and β-$(H_3N(CH_2)_2NH_3)[V_4O_{10}]$, $(HN(C_2H_4)_3NH)[V_6O_{14}]\cdot H_2O$, α- and β$(H_2N(C_2H_4)_2NH_2)[V_4O_{10}]$.

The third group corresponds to the situation where a=0, and both b and c have real values in the generic formula, so that both $M_2$ and $M_3$ are included.

An example of this group is $Cs_{0.29}(DABCO)_{0.34}V_2O_5$ where DABCO is diprotonated 1,4-Diazabicyclo[2.2.2]octane $N(C_2H_4)_3N$. Samples of this were prepared by heating at 170° C. for 112 hours a mixture of 0.202(g) $CsVO_3$, 0.312(g) $H_2O_3PCH_3$, 10(ml) $H_2O$ and 0.310(g) DABCO. Other members of this group can be formed by including cations from the others of the alkali metal group, $K^+$ or $Rb^+$.

The following are additional examples of the preparation of further representatives of the general class.

A mixture of 0.277 grams of $V_2O_5$, 0.049 gram of CuO, 10 milliliters of water and 0.3 milliliter of $H_2N$—$CH_2$—$CH_2$—$CH_2$—$NH_2$(dap) was heated at 170° C. and after 44 hours 0.118 grams of a solid was recovered after filtering, washing and air-drying. The solid was found to be of the following composition: $(dap)_2Cu[V_6O_{14}]$, a member of the first group.

A mixture of 0.130 gram of $V_2O_3$, 0.197 gram of piperazine and 10(ml) water was heated at 170° C. After 67 hours, and after filtering, water washing and air drying there was recovered 0.122 gram of a solid whose composition was found to be $(H_2N(CH_2CH_2)_2NH_2)[V_4O_9]$, a member of the second group.

A mixture of 0.218 gram of $V_2O_5$, 0.181 gram of piperazine and 10 milliliters of water was heated at 170° C. and after 115 hours there was recovered 0.152 gram of a solid whose composition was found to be a mixture of α- and β-phase of $(H_2N(CH_2CH_2)_2NH_2)[V_4O_{10}]$, a member of the second group.

A mixture of 0.173 gram of $V_2O_5$, 0.1 milliliter of en and 10 milliliters of water was heated at 170° C. and after 121 hours there was recovered 0.10 gram of a solid whose composition was found to be a mixture of α- and β- phase of $(H_3NCH_2CH_2NH_3)[V_4O_{10}]$, also a member of the second group.

A mixture of 0.257 gram of $CsVO_3$, 0.186 gram of $H_2O_3PCH_3$, 0.1 milliliter of en and 8 milliliters of water was heated at 170° C. and after 69 hours there was recovered 0.075 gram of a solid whose composition was found to be a mixture of α- and β-phase of $(H_3NCH_2CH_2NH_3)[V_4O_{10}]$, a member of the second group.

A mixture of 0.225 gram of $V_2O_5$, 0.201 gram of DABCO and 10 milliliters of water was heated at 170° C. and after 45 hours there was recovered 0.127 gram of a solid whose composition was found to be $(HN(C_2H_4)_3NH)[V_6O_{14}]\cdot H_2O$, another member of the second group.

A mixture of 0.192 gram of $V_2O_5$, 0.042 gram of ZnO, 10 milliliters of water and 0.2 milliliter of en was heated at 170° C. and after 66 hours there was recovered 0.187 gram of a solid whose composition was found to ben $(en)_2Zn[V_6O_{14}]$, a member of the first group.

A mixture of 0.5 gram of nickel acetate, 0.181 gram of $V_2O_5$, 0.45 milliliter of ethylenediamine and 8.0 milliliters of water was heated to 200° C. After 74 hours, there was recovered a cluster of black crystals of $(en)_2Ni[V_6O_{14}]$, another member of the first group.

A mixture of 0.51 gram of copper chloride dehydrate, 0.181 gram $V_2O_5$, 0.45 milliliter of ethylenediamine and 8.0 milliliters of water was heated at 170° C. After 42 hours, there was recovered crystals of $[(en)_2Cu]_2[V_{10}O_{25}]$, also a member of the first group.

A mixture of 0.17 gram of copper chloride dihydrate, 0.181 gram of $V_2O_5$, 0.28 milliliter of ethylenediamine was heated to 170° C. After 65 hours, there was recovered 0.1743 gram of $(en)_2Cu[V_6O_{14}]$, also of the first group.

A mixture of 0.34 gram of copper chloride dihydrate, 0.181 gram of $V_2O_5$, 0.8 milliliter of ethylenediamine and 8.0 milliliters of water was heated to 125° C. After 68 hours there was recovered 0.215 gram of a solid of which most was $(en)_2Cu[V_6O_{16}]$ and some was $(en)Cu[V_2O_6]$, members of the first group.

What is claimed is:

1. A layered vanadium oxide composition having the formula $(H_3N(CH_2)_3NH_3)[V_4O_{10}]$.

* * * * *